United States Patent
Sperling et al.

(10) Patent No.: US 8,734,317 B2
(45) Date of Patent: May 27, 2014

(54) METHOD TO IMPROVE CONCENTRATION AND/OR MEMORY IN A SUBJECT IN NEED THEREOF

(75) Inventors: Michael R. Sperling, Bryn Mawr, PA (US); Joseph I. Tracy, Lawrenceville, NJ (US); Young Hyun Lim, Seoul (KR)

(73) Assignees: Thomas Jefferson University, Philadelphia, PA (US); Young Hyun Lim, Seoul (KR)

( * ) Notice: Subject to any disclaimer, the term of this patent is extended or adjusted under 35 U.S.C. 154(b) by 876 days.

(21) Appl. No.: 12/126,193

(22) Filed: May 23, 2008

(65) Prior Publication Data

US 2009/0023977 A1    Jan. 22, 2009

Related U.S. Application Data

(60) Provisional application No. 60/940,153, filed on May 25, 2007.

(51) Int. Cl.
A61M 21/00    (2006.01)

(52) U.S. Cl.
USPC .............................. 600/27; 434/236; 434/323

(58) Field of Classification Search
USPC .......... 600/300, 27; 607/88, 90; 434/236, 323
See application file for complete search history.

(56) References Cited

U.S. PATENT DOCUMENTS

| | | | |
|---|---|---|---|
| 4,289,121 A * | 9/1981 | Kupriyanovich | ............... 600/27 |
| 4,315,502 A | 2/1982 | Gorges | |
| 5,036,858 A * | 8/1991 | Carter et al. | ................... 600/545 |
| 5,163,426 A * | 11/1992 | Czeisler et al. | ................. 607/88 |
| 5,304,112 A * | 4/1994 | Mrklas et al. | ................... 600/27 |
| 5,518,497 A * | 5/1996 | Widjaja et al. | ................... 600/27 |
| 6,443,977 B1 * | 9/2002 | Jaillet | ............................. 607/88 |
| 2002/0047646 A1 * | 4/2002 | Lys et al. | ...................... 315/312 |
| 2002/0198577 A1 | 12/2002 | Jaillet | |
| 2004/0095746 A1 * | 5/2004 | Murphy | .......................... 362/86 |
| 2004/0230252 A1 | 11/2004 | Kullok et al. | |
| 2005/0244797 A9 * | 11/2005 | Klingberg | ..................... 434/236 |

OTHER PUBLICATIONS

Lee SH, Kim JH, Park JK, Lee KU, Yang DH, Hong KY, Chae JH. "The Changes of Short Term MEmory and Autonomic Neurocardiac function after 4-10 Hz Sound and Light Stimulation." Sleep Medicine and Psychophysiology 11(1) 29-35, 2004.*
S. Lee et al., "The Changes of Short-Term Memory and Autonomic Neurocardiac Function after 4-10Hz Sound and Light Stimulation—A Pilot Study," *Sleep Medicine and Psychophysiology*, vol. 11, No. 1, pp. 29-36, 2004. Abstract.
Tracy, Joseph I., et al. "A test of the efficacy of the MC Square device for improving verbal memory, learning and attention", Int. J. Learning Technology, vol. 3, No. 2, 2007, pp. 183-202.

* cited by examiner

*Primary Examiner* — Christine Matthews
*Assistant Examiner* — Joshua D Lannu
(74) *Attorney, Agent, or Firm* — Nixon Peabody LLP; David S. Resnick; Robert L. Pilaud

(57) ABSTRACT

The present invention is directed to a method of treatment to improve at least one of concentration, memory, cognitive performance, and stress-relief in a subject in need thereof by controlled administration of synchronized flashes of light and pulsed tones.

17 Claims, 1 Drawing Sheet

METHOD TO IMPROVE CONCENTRATION AND/OR MEMORY IN A SUBJECT IN NEED THEREOF

CROSS-REFERENCE TO RELATED APPLICATIONS

The present application claims the benefit under 35 U.S.C. §119(e) of provisional application No. 60/940,153, filed May 25, 2007, the content of which is herewith incorporated by reference in its entirety.

FIELD OF THE INVENTION

The present invention relates to a method of treatment to improve concentration and/or memory in a subject in need thereof.

BACKGROUND OF THE INVENTION

In modern society there is an increased focus on academic achievement. This competitive environment has lead to a growing demand for learning tools that will aid and enhance performance on standardized achievement or ability tests, employment/civil service tests, or for those seeking admission to advanced schooling such as undergraduate or graduate school. In addition, cognitive enhancement tools are also sought for rehabilitation after brain injury following stroke, head trauma, or other brain insults. Many of these cognitive enhancement devices have positive anecdotal reports behind them, but have not undergone rigorous testing to determine if they yield any actual cognitive benefit.

The present invention is directed to overcoming these and other deficiencies in the art.

SUMMARY OF THE INVENTION

The present invention is directed toward a method of treatment to improve at least one of concentration, memory, cognitive performance, and stress-relief by audio-visual entrainment comprising selecting a subject in need of improvement in at least one of concentration, memory, cognitive performance, and stress-relief and administering synchronized flashes of light and pulsed tones to the subject, wherein the synchronized flashes of light and pulsed tones are in the frequency range of 4-12 Hz.

DETAILED DESCRIPTION OF THE INVENTION

Figure 1A:
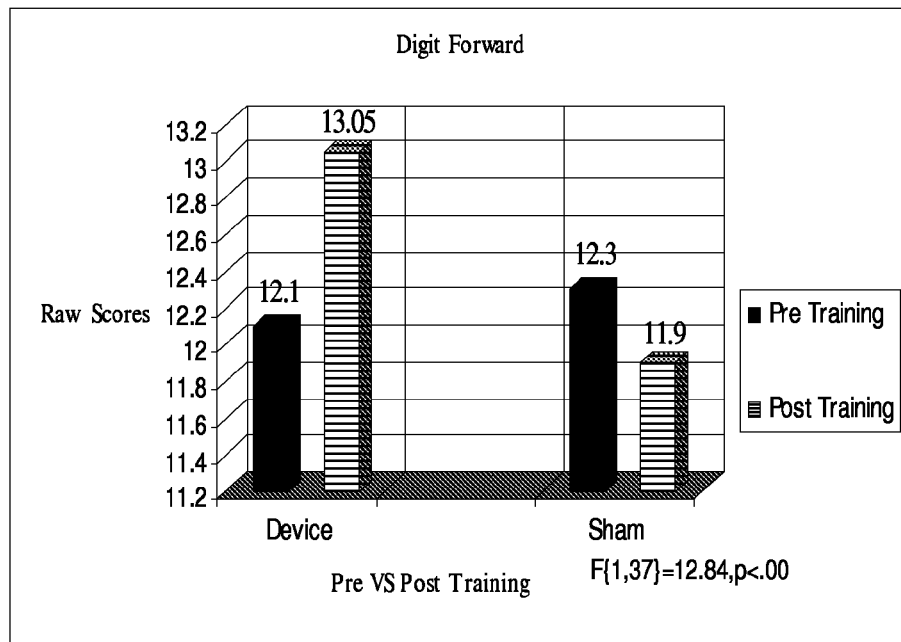
FIGS. 1A-B show graphs of the raw and error corrected pre- and post-training scores for MC Square device and sham device for the Digit forward (FIG. 1A) and the Total Digit Span (FIG. 1B) scores.

One aspect of the present invention is directed toward a method of treatment to improve at least one of concentration, memory, cognitive performance, and stress-relief by audio-visual entrainment comprising selecting a subject in need of improvement in at least one of concentration, memory, cognitive performance, and stress-relief and administering synchronized flashes of light and pulsed tones to the subject, wherein the synchronized flashes of light and pulsed tones are in the frequency range of 4-12 Hz.

The method may also include flashes of light having a wavelength in the range of 400 to 720 nm and a brightness in the range of 0 to 16 Lx. The flashes of light may include a wave form with a varying frequency or a constant frequency.

The varying frequency may include at least one of an ascending frequency and a descending frequency. The flashes of light and pulsed tones may be administered in-phase (e.g. both sides (left and right channels) are in synch: the light and sound are generating at the same time at the left and right), out-phase (e.g. both sides (left and right channels) are out of synch: when one channel is on, the other one is off, alternating each other), or a combination or mixture thereof. The flashes of light and pulsed tones may be administered, for example, for a period of 15 to 60 minutes or may be administered for example, for a period of 15 to 30 minutes. The flashes of light and pulsed tones may be administered for example, daily for three or more days.

The subject in need of treatment to improve at least one of concentration, memory, cognitive performance, and stress-relief may be diagnosed with ADHD or may be suffering from age-related memory loss or be at risk for age-related memory loss. The subject may have significant difficulty focusing or concentrating. The subject may have developmental impairment of executive function. The subject may need treatment to improve cognitive performance in areas including but not limited to, standardized or other educational tasks or testing or occupational tasks or testing.

In one embodiment, the method may comprise administering sounds of nature. For example, the sounds of nature may include at least one of river gurgling, birds chirping, rain drops, and ocean waves or other relaxing sounds.

In another embodiment, the method includes establishing a baseline score for at least one of concentration, memory, cognitive performance, and stress-relief for the subject prior to administering the synchronized flashes of light and pulsed tones and measuring an improved score for at least one of concentration, memory, cognitive performance, and stress-relief for the subject after administering the synchronized flashes of light and pulsed tones.

In another embodiment, stress-relief includes at least one of increasing relaxation, decreasing anxiety, and increasing restorative sleep.

In yet another embodiment, an audio-visual stimulation device is used. Those skilled in the art will recognize that the method may be practiced utilizing a variety of appropriately configured devices, non-limiting examples include phone, PDAs, MC Square, or other electronic devices known in the art. The device may be hand held or stand alone. Such a device includes synchronized flashing lights and pulsed tones. The flashing lights and pulsed tones are synchronized at a selected frequency or programmed to vary frequency following an ascending pattern, a descending pattern, or a combination of ascending and descending.

In still another embodiment, the method comprises software and or programming in devices known in the art.

In one embodiment the synchronized flashes of light and pulsed tones are achieved using an MC Square device. The MC Square was developed by Daeyang E & C, Inc. of Seoul, Korea. This device utilizes synchronized sound and light to entrain brain waves to alpha and theta neural rhythms. The device uses a series of flashing red lights in conjunction with pulsed tones and background relaxing sounds (e.g. river gurgling, birds chirping, rain drops, ocean waves) to achieve its effects. The lights are presented through an eye goggle device that resembles a thick pair of eye glasses. Light emitting diodes present red light that appear as flickering dots which occur synchronously with pulsed tones at a rate and pattern to induce alpha and theta brain wave activity.

This technique of inducing alpha and theta waves of brain by audio-visual stimulation (AVS) is known as brain wave entrainment or audio-visual entrainment (AVE). AVE has been demonstrated to cause significant changes in EEG patterns and cerebral synchronization. Scientific research examining the effects of light and sound started in mid-1930s when scientists discovered that the electrical rhythm of brain tended to adopt the frequency of light when this is used as external stimulation. In one of the earliest reports, Adrian and Matthew (Adrian & Matthews, 1934) confirmed that alpha rhythm can be driven above and below the natural frequency by photic stimulation. Flickering light appears to share some similarity in terms of frequency with brain waves in the alpha and theta range. Manufacturers of light and sound devices have almost exclusively used red light-emitting diodes because they are bright, inexpensive, and blood vessels in the eyelids pass red/orange light most efficiently. Komatsu (Komatsu, 1987) examined college students and found that red light produces optimal EEG driving it in the 17-18 Hz band. Green increases brain wave activity to 15 Hz, blue light enhances 10-13 Hz activity, and white light peaks at 18-19 Hz. AVE has been associated with increases in cerebral blood flow (Fox & Raichle, 1985) (Sappey-Marinier et al., 1992) and this is thought to be one of the mechanism by which it entrains brain waves to the alpha and theta state as measured by EEG. Fox and Raichle (Fox & Raichle, 1985) showed that photic stimulation at alpha and low beta frequencies increased cerebral blood flow 20-30% over baseline in the striate cortex. Moreover, certain parameters of the EEG tend to correlate with cerebral perfusion at least in the neocortex (Fried, 1993). Hypoperfusion will tend to be mirrored by the increase of theta band (4-8 Hz) power in the EEG on the scalp surface in that location. Reductions in cerebral perfusion has been shown to decrease with age and in elderly individuals generally, with some signs that the effect may be more pronounced in the elderly who show cognitive deficits (Schreiter-Gasser, Gasser, & Ziegler, 1993). One well-demonstrated effect of AVS is relaxation. This effect may arise from high sympathetic activation that occurs during alpha state. EMG correlates of relaxation have been observed in individuals undergoing AVS (Manns, Miralles, & Adrian, 1981).

Alpha and theta brain waves are considered optimal for learning and attention and there have been attempts to induce these states to reduce memory problems and regain cognitive function. Several studies have shown that there is a strong relationship between peak alpha rhythm and mental performance (Jausovec, 1996). Klimesch (Klimesh, Doppelmayr, Pachinger., & Ripper, 1997) presented evidence that EEG oscillations in the alpha and theta band reflect cognitive and memory performance in particular. A peak alpha rhythm of less than 10 HZ is associated with poorer academic performance and an alpha rhythm frequency of more than 10 HZ is associated with better performance (Jausovec, 1996). Budzynski and Tang (T. H. Budzynski & Tang, 1998) colleagues collected EEG in a sample of college students and subdivided alpha rhythms (9-13 Hz) into three categories (A1, 7-9; A2, 9-11; A3, 11-13) and examined whether the ratio between A3/A1 predicted academic performance. A ratio value above 1.0 was associated with above average academic performance. They also found that after 34 sessions of 14 HZ light stimulation the high-to-low alpha frequency ratio was increased along with an increase in peak alpha frequency. In a later study by Budzynski (T. Budzynski, Jordy, Budzynski, Tang, & Claypoole, 1999) again with college students, they found that following 30 sessions of repeated cycles of AVE at 22 Hz and 14 Hz in an alternating pattern, there was a significant increase in the mean A3/A1 ratio, alpha rhythm, and academic performance. This positive ratio was also related to improved cognitive performance as measured by a digit span task. Budzynski and Tang (Budzinski, Budzinski, Sherlin, & Tang., 2002) used AVE (a Digital Audio-Visual Integration Device, Paradise XL) to aid 31 elderly individuals who were experiencing cognitive problems. The AVE session utilized random frequency stimulation from 9-22 Hz and an average of 33 treatment sessions took place. The treatment was considered very cost effective because 10 individuals could be treated at one time. A computer-based Continuous Performance Test and the Microcog Test Battery were utilized to assess cognitive change. The Microcog measures several domains of cognitive function including attention, reasoning ability, memory, spatial ability, processing speed & accuracy, and cognitive proficiency. Over 60% of participants showed improvement in at least some of the cognitive measures. This AVE procedure has also been shown to improve cognitive functioning in certain clinical populations such as dementia (Tan, Kelly, & Calhoun, 1997) and dyslexia (Magnan, Ecalle, Veuillet, & Collet, 2004). Other studies with AVE devices have suggested beneficial effects may be observed in behavior and psychiatric symptoms such as depression (Kumano et al., 1996; Rosenfeld, 1997)premenstrual syndrome (David, 1997) and attention deficit disorder (Cohen & Douglas, 1972) (Zentall & Zentall, 1976).

In Example 1, we investigated the cognitive efficacy of the MC Square device, to examine its affect on major domains of cognitive functioning. Verbal material was chosen, since informal reports from users of the device suggested that it produces gains in the acquisition and retention of verbal material such as might be required when studying for an academic exam. As practice with the device was also reported to be superior to single instance use, we implemented week long device use in testing it. A sham device was constructed to create a placebo arm of the study whereby participants were run through the identical procedure without the key element of the MC Square device; that is the sham device used randomized not synchronized light and sound.

Our hypotheses were as follows: (1) after training with the MC Square Device there would be improvement in verbal memory, associative learning, working memory and attention/concentration. The sham device will produce no such training effect. (2) On individual performance measures, pre- or post-training, the MC Square Device would be associated with better performance than the sham device.

The above cognitive tasks involve novel material that requires effort, cognitive resources, and cognitive skill to complete successfully. In contrast, Vocabulary items involving over-learned, highly familiar material that require no new learning and fewer cognitive resources to complete successfully were used as a control task. These multiple-choice vocabulary items called upon existing, readily available knowledge. Therefore, hypothesis three was that neither training on the MC Square nor the sham would produce improvement in Vocabulary.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean ±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLE

Method

Participants were recruited by advertisements at Thomas Jefferson University. All participants for this study were screened for good general health and the absence of any neurological, psychiatric or medical disorder. A questionnaire was constructed to eliminate individuals with photosensitive seizures, i.e., seizures in response to light stimulation. A total of 120 normal, healthy adult subjects within the 18-45 age range were screened to enroll 40 subjects. All subjects were native English speakers with at least an Average IQ (90 or greater) based on the Shipley Hartford Institute for Living Scale. All participants were medical students, physical therapy or PhD students, residents and nurses from Thomas Jefferson University. Ineligibility arose from having IQ below 90, abnormal state or trait anxiety scores on the Spielberger Inventories, and prior medical or psychiatric history with potential central nervous system impact (e.g., neurological or medical condition with central nervous system impact, depression, anxiety, substance abuse, obsessive-compulsive disorder, and migraines; 70 individuals). Six individuals were dropped because of time and scheduling constraints. Three individuals were dropped because of IQ less than 89, and one because of risk of photosensitive seizures. This produced a final enrollment sample of 40 subjects. One subject dropped out in the middle of the study due to scheduling conflicts. This yielded a final analytic sample of 39.

Sample demographics can be seen in Table One. The sample primarily was Caucasian though some mixed ethnicity was present. The sample was well educated and of Above Average IQ. As the MC Square device might induce relaxation, we sought to reduce the differential and beneficial effect this might have across individuals by limiting our sample to individuals who showed clearly average range (i.e., low) levels of state and trait anxiety as measured by the Spielberger Inventory (Spielberger, Gorsuch, & Lushene, 1970).

TABLE 1

Demographic Baseline Screening Data

| Mean age | 25.60 (S.D of 5.21) |
| Males | 22 |
| Females | 18 |
| Mean Education | 16.90 (S.D of 2.37) |

TABLE 1-continued

Demographic Baseline Screening Data

| Ethnicity | Black (8), Caucasian (26), Asian (6) |
| Mean IQ | 112.30 (S.D of 7.19) (Shipley Hartford Scale estimate) |
| | Speilberger Anxiety Scales |
| State | −0.4 Z score (S.D of .516) - Normal range |
| Trait | 0.11 Z score (S.D of .785) - Normal range |

Research Design

The study utilized a double blind, placebo controlled, and crossover design. Within each element of the crossover (MC Square device, Sham) participants underwent pre-testing on the cognitive measures, training with the device, then post-testing on the same cognitive measures. Participants undertook baseline testing (3 hours) of the neurocognitive skills under investigation without the MC Square device. The baseline testing included screening materials such as the The Shipley Hartford Institute of Living Scale for assessment of IQ (Robert, 2001), and the Spielberger State and Trait Anxiety Scales for determining baseline levels of anxiety. Other measures in this first session included the initial assessments of Memory (Hopkins Verbal Learning Test) (Jason, 2001), Verbal Learning (Paired Associate subtests from the Wechsler Memory Scale, WMS, with versions III, R, and the original WMS were used in order to obtain 5 versions), Working Memory (Letter Number Sequencing subtest from the WMS-III with additional versions constructed), (D. Wechsler, 1997, b) Attention (Digit Span subtest from the WMS-III with additional versions constructed), and Vocabulary (multiple choice practice PSAT and SAT items, with the 5 versions equated for difficulty by pre-testing with a separate sample of 10 individuals. All five versions were completed with the mean scores within two points of each other).

Participants underwent cognitive testing with initial use of the MC Square Device or Sham on Day 1. Post-testing with the cognitive tests took place on Day 8. During the intervening period participants practiced for 15-20 minutes each day at home with the MC Square device or Sham depending on the experimental condition. A log book and sworn statement was used to attest to their practice with the device. A second identical testing session was held on Day 15 (pre-test) and Day 22 (post-test) with the device not utilized during the first session. Participants were randomly assigned in a counterbalanced fashion to one of two experimental session orders, e.g., Sham (day 1 pre-test, day 8 post-test) then the active MC Square device (day 15 pretest, day 22 post-test), or the opposite order—active MC Square then the Sham device. During days 9 though 14 participants were given a break and did not utilize the MC Square device or Sham. All pre and post-test sessions utilized the device and followed the sequence of events depicted in Table 2. A post-doctoral research fellow administered the cognitive tests and remained blind to participant assignment. In total, participants attended five sessions: baseline (3 hours), session one pre-test and post-test, and session two pre-test and post-test. The pre and post-test sessions took approximately two and a half hours. The blind was broken at the end of the last session for the last subject after scoring and final entry of all data.

TABLE 2

Experimental Design and Sequence of Events

| Order | Baseline Assessment | Experimental Session 1 | | | 6 Days interval | Experimental Session 2 | | |
|---|---|---|---|---|---|---|---|---|
| | | Day 1 | Day 2-7 | Day 8 | | Day 15 | Day 16-21 | Day 22 |
| Mc Sq/Sham | Health History, Photosen. Epilepsy Qnaire. Shipley Speilberger HVLT Digit Span VPA LNS Vocabulary | MC Square p2, p1 mode HVLT Learning Trials Digit Span HVLT-DR MC Sq p-1 VPA LNS VPA-DR MC Sq p-1 Vocabulary | MC Square at home or work (two times per day) | MC Square p2, p1 mode HVLT, 123 Learning Trials Digit Span HVLT-DR MC Sq p-1 VPA LNS VPA-DR MC Sq p-1 Vocabulary | Break | Sham device p2, p1 mode HVLT, 123 Learning Trials Digit Span HVLT-DR MC Sq p-1 VPA LNS VPA-DR MC Sq p-1 Vocabulary | Sham Device at home or work (two times per day) | Sham device p2, p1 mode HVLT, 123 Learning Trials Digit Span HVLT-DR MC Sq p-1 VPA LNS VPA-DR MC Sq p-1 Vocabulary |
| Sham/Mc Sq | Qnaire. Shipley Speilberger HVLT Digit Span VPA LNS Vocabulary | Sham device p2, p1 mode HVLT, 123 Learning Trials Digit Span HVLT-DR MC Sq p-1 VPA LNS VPA-DR MC Sq p-1 Vocabulary | Sham Device at home or work (two times per day) | Sham Device p2, p1 mode HVLT, 123 Learning Trials Digit Span HVLT-DR MC Sq p-1 VPA LNS VPA-DR MC Sq p-1 Vocabulary | Break | MC square p2, p1 mode HVLT, 123 Learning Trials Digit Span HVLT-DR MC Sq p-1 VPA LNS VPA-DR MC Sq p-1 Vocabulary | MC Square at home or work (two times per day) | MC Square p2, p1 mode HVLT, 123 Learning Trials Digit Span HVLT-DR MC Sq p-1 VPA LNS VPA-DR MC Sq p-1 Vocabulary |

MC Square Device Characteristics

The MC Square device has different modes of operation, but only two modes were used in this study. The P-1 mode is for concentration enhancement and set at an alpha frequency (8-12 Hz) throughout the study. The P-2 mode is for inducing relaxation and is set at a combination of alpha and theta frequencies (4-12 Hz range), beginning with alpha, then theta (4-8 Hz), and then ending in alpha. The device works much like a small hand held radio. The choice of modes was easily set by a dial on the surface of the device. The device generated pulsed tones in the frequency range of 4-12 Hz (the range of theta and alpha waves), which was always synchronized at the same frequency as the flickering light. In the background, nature sounds were presented. The brightness of the flickering light, the volume of the tone pulses, and the volume of the background nature sounds was adjustable. The rate of flickering of the light and the rate of pulsing for the tones was not adjustable and determined by the P-1 and P-2 modes. There were 4 light diodes per eye set at a flickering rate of 4-12 Hz with a wavelength of 400 to 720 nm and brightness in the range of 0 to 16 Lx. The diodes emitted red light, and as noted earlier this is because blood vessels in the eyelids pass red/orange light most efficiently. The volume of the pulsed tones was allowed to be adjustable and customized to the subject so as to avoid aversive loudness. The frequency set to alpha and theta, and the synchronization of flickering lights and tones were considered the major though not the sole ingredient of effective brain wave entrainment through the MC Square device.

So that any observed effect could be reliably attributed to one variable, it was decided that the Sham would be identical to the MC Square device with the exception of the frequency. The rate (frequency) of the flickering light and the synchronized pulsed tone was randomized and never settled into an alpha, theta or other range reliably for more than one second. Also, so as not to potentially eliminate a characteristic that may contribute to the MC Square's effectiveness, all other aspects associated with typical use of the device were maintained (e.g. background audio track for relaxation).

Thus, the Sham device looked, felt, and operated identically to the active MC Square device with the exception that the light and tone pulses were presented in a random, though synchronized, fashion and did not utilize a wavelength entrainment algorithm.

During each pre- and post-test session the MC Square or Sham device was administered four times. The order of events in the pre- and post-test sessions is depicted in Table 3. The device was kept in P-2 mode for the first or initial use at each session then changed to P-1 mode for all subsequent uses. Subjects utilized the P-1 mode during practice sessions at home.

Pre- and Post-Test Measures

Four areas of neurocognitive functioning were assessed: Verbal Episodic Memory, Verbal Associative Learning, Verbal Working Memory, and Attention/Concentration. Two of the tests utilized to assess these domains had five versions available (Hopkins Verbal Learning Test, Paired Associates Learning Test). Additional versions were constructed for the remaining tests (Vocabulary, Digit Span Forwards and Backwards, and Letter Number Sequencing). A control task was developed, assessing vocabulary skills through a multiple choice format. Pre-test and post-test sessions were identical with the exception of the particular test version utilized. All tests with the exception of the Vocabulary test were well-established, well-normed neuropsychological instruments. Administration and scoring procedures followed the standardized procedure described in the test manuals.

Verbal Episodic Memory:

The Hopkins Verbal Learning Test (Jason, B, 2001) was used as a measure of verbal episodic memory. This test consists of three learning trials composed of 12 individual words. A Delayed Recall of the words was taken 20-25 after the third learning trial. A Delayed Recognition trial was then administered composed of the 12 target words plus 12 non-target (non-heard) distracters. A Total Learning score (HVLT-TR) based on the 3 learning trials, a Delayed Recall score (HVLT-DR) score, Delayed Recognition Index (HVLT-RDI), and a Percent Retention score (HVLT-PR) were computed according to the manual and utilized in the analyses.

Verbal Associative Learning:

The Verbal Paired Associates subtest of the Wechsler Memory Scale-III (Wechsler, D. 1997,b) was used as a measure of verbal learning. In this test there were a total of eight word pairs. After the word pairs were read aloud, participants were given the first word in the pair and required to provide the second. The set of 8 word pairs was given and tested 4 times in each session. After 25-30 minutes a delayed recall test was given where again only the first word of the pair was given and participants had to provide the second word in the pair. A final delayed recognition phase was administered at each session. Here, participants were read the eight word pairs randomly interspersed among 16 non-target (non-heard) pairs and participants had to identify the correct pair. Note, only non-semantically related word pairs were utilized. By utilizing past versions of the Wechsler Memory Scale (version III, Revised, and original, five versions of this tests were created). A Total Learning score (VPA-TL) based on the 4 learning trials was computed in addition to a Learning Slope score (VPA-LS), Total Delayed Recall score (VPA-TDR), a Percent Retention score (VPA-PR), and a Total Delayed Recognition score (VPA-DRecog.).

Verbal Working Memory:

The Letter Number Sequencing subtest of the Wechsler Memory Scale-III (Wechsler, D, 1997,b) was utilized as the measure of verbal working memory. Participants were given series of random letters and numbers. The subject was required to repeat back the numbers in their cardinal (ascending) order and the letters in alphabetical order. The string of letters and numbers became increasingly longer with each trial. The subjects proceeded until they failed three times at a given letter/number span. A total of 21 trials were administered, two at each span with a maximum span of 8 items (4 letters, 4 numbers). Additional versions of this test were developed simply by utilizing strings of random numbers and letters with no repetition of any string. The Total Score (LN-Sequencing) reflecting the number of correct trials was utilized in the analyses.

The Digit Span Backwards subtest of the Wechsler Memory Scale-III was used as a second measure of verbal working memory. The task is identical to the Digit Span Forward subtest described above with the exception that the participant had to recite the digits backwards, opposite the heard order. Additional versions of this test were developed simply by utilizing strings of random numbers. The Total Digits Backward score was in used in the analyses.

Attention/Concentration:

The Digit Span (Forward) subtest of the Wechsler Memory Scale-III (Wechsler, D. 1997,b) was used as a measure of auditory attention. The subject is required to repeat back a given string of digits, with each series of digits becoming increasingly longer. The subjects proceed until they fail twice at a given digit span. There were 16 trials, 2 at each span with a maximum span of 9 digits. Additional versions of this test were developed simply by utilizing strings of random numbers. The total Digits Forward raw score was used in the analysis.

Control Task:

A multiple choice Vocabulary test was used as a control task. It measures semantic knowledge. These items were taken from preparatory books for standardized college entrance exams (PSAT, SAT). Target items were presented with four choices and participants had to identify the synonym or word closest in meaning to the target word. Pretesting was used to develop 5 equivalent 50-item versions. As noted, improvement via the MC Square device was not expected for this measure.

Statistical Analyses

Statistical analyses involved a repeated measures analysis of variance on the pre and post test scores of the two sessions with two within-subject factors both two-level in nature: Session (First, Second), Training Condition (pre-test, post-test). Order (MC Square condition then Sham, or vice versa) served as a between subject factor. Additional analyses of variance were run on pre or post-test scores with Experimental Condition (MC Square, Sham) and Session (First, Second) as between-subject factors. All analyses were subject to Type I error correction using the Bonferroni method for 14 tests. An observed alpha of $p<0.001$ was required to maintain an effective alpha of $p<0.05$.

Results

The sample mean scores and standard deviation for each measure are shown in Table 3. We will first examine the effect of training with the MC Square device by focusing on the Repeated Measures Analysis. Here, the key effect in the model testing the hypothesis of improved performance following MC Square training involves the interaction between Session, Training Condition, and Order. The statistical results for the Repeated Measures Analysis are shown in Table 4.

TABLE 3

Pre- and Post-Training Means and Standard Deviations of Cognitive Measures During MC Square and Sham Conditions

| Condition | | HVLT-TR | | HVLT-DR | | HVLT-PR | |
|---|---|---|---|---|---|---|---|
| | | Pre | Post | Pre | Post | Pre | Post |
| Mc Sq. | Mean | 50.3 | 52.8 | 50.5 | 53.8 | 48.8 | 50.5 |
| | sd | 9.6 | 7.6 | 11.6 | 8.1 | 10.9 | 8.7 |
| Sham | Mean | 50.7 | 51.7 | 49.4 | 50.4 | 47.3 | 49.2 |
| | sd | 8 | 10.2 | 10.7 | 10 | 10.4 | 8.9 |

| Condition | | HVLT-RDI | | VPA-TL | | VPA-TDR | |
|---|---|---|---|---|---|---|---|
| | | Pre | Post | Pre | Post | Pre | Post |
| Mc Sq. | Mean | 50.9 | 54.4 | 23.8 | 25.5 | 7.1 | 7.5 |
| | sd | 9.4 | 6.8 | 6.7 | 5.4 | 1.5 | 1.2 |

TABLE 3-continued

Pre- and Post-Training Means and Standard Deviations of Cognitive Measures During MC Square and Sham Conditions

| Sham | Mean | 51.5 | 51.9 | 24.1 | 24.4 | 7.3 | 7.3 |
|---|---|---|---|---|---|---|---|
|  | sd | 8.4 | 8 | 6 | 5.8 | 1.2 | 1.4 |

|  |  | VPA-LS | | VPA-PR | | VPA-DRecog. | |
|---|---|---|---|---|---|---|---|
| Condition | | Pre | Post | Pre | Post | Pre | Post |
| Mc Sq. | Mean | 3.7 | 3.1 | 96.7 | 97.3 | 24 | 24 |
|  | sd | 1.9 | 1.8 | 17.3 | 7.7 | 0 | 0 |
| Sham | Mean | 3.8 | 4 | 99.5 | 99.5 | 24 | 24 |
|  | sd | 2 | 1.8 | 9 | 10.05 | 0 | 0 |

|  |  | LN-Sequencing | | Digit Forward* | | Digit Backward | |
|---|---|---|---|---|---|---|---|
| Condition | | Pre | Post | Pre | Post | Pre | Post |
| Mc Sq. | Mean | 13.3 | 14.8 | 12.1 | 13.05 | 9.4 | 10.5 |
|  | sd | 3 | 2.7 | 2 | 1.6 | 2.9 | 2.7 |
| Sham | Mean | 12.9 | 13.3 | 12.3 | 11.9 | 9.6 | 9.5 |
|  | sd | 2.6 | 2.8 | 1.9 | 2.3 | 2.2 | 2.7 |

|  |  | Total Digit Span* | | Vocabulary | |
|---|---|---|---|---|---|
| Condition | | Pre | Post | Pre | Post |
| Mc Sq. | Mean | 21.5 | 23.7 | 34.2 | 34 |
|  | sd | 4.1 | 4.1 | 5.7 | 5.6 |
| Sham | Mean | 22.1 | 21.4 | 34.05 | 34.5 |
|  | sd | 3.7 | 4.6 | 6.1 | 5.8 |

Legend for Table 3:
Hopkins Verbal Learning Test-Total Recall (HVLT-TR)
Hopkins Verbal Learning Test-Delayed Recal (HVLT-DR)
Hopkins Verbal Learning Test-Percent Retention Score (HVLT-PR)
Hopkins Verbal Learning Test-Recognition Discrimination Index (HVLT-RDI)
Verbal paired Associates-Total Learning (VPA-TL)
Verbal paired Associates-Total Delayed Recall (VPA-TDR)
Verbal paired Associates-Learning Slope (VPA-LS)
Verbal paired Associates-Percent Retention (VPA-PR)
Verbal paired Associates-Delayed Recognition (VPA-DRecog.)
Letter Number Sequencing - (LN-Sequencing)
*Statistically significant pre/post difference after Bonferroni Correction.

Figure 1B:
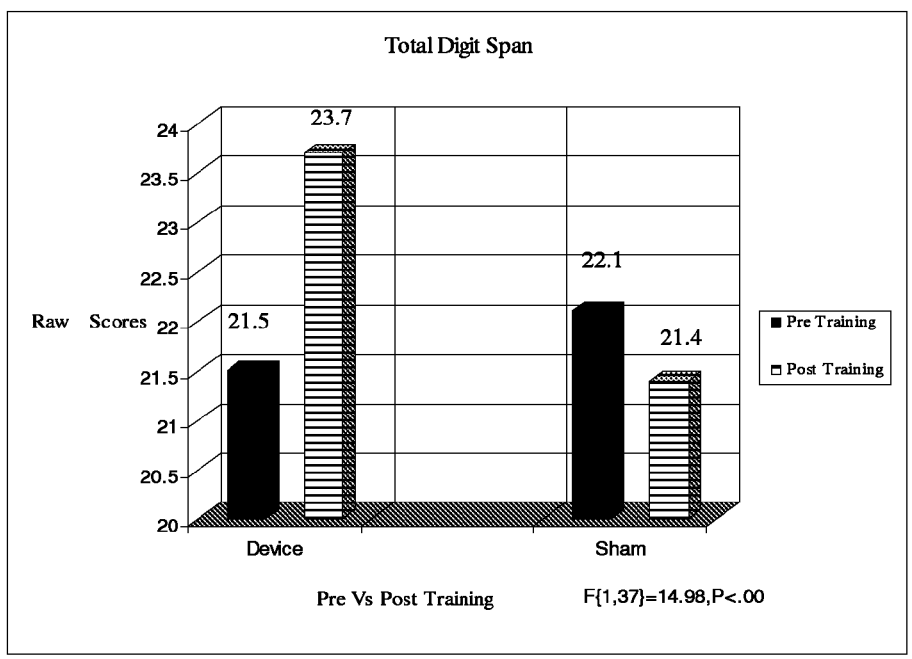

Of the 14 Repeated Measures Analyses of Variance the triple interaction of Session, Training Condition, and Order was significant for Verbal Paired Associates Total Recall ($F\{1,37\}=6.975$, $p<0.05$), Digits Forward ($F\{1,37\}=12.846$, $p<0.01$) and Backwards ($F\{1,37\}=6.104$, $p<0.05$), and Total Digit Span ($F\{1,37\}=14.988$, $p<0.1$). In each instance the difference between the pre- and post-training scores was greater in the MC Square condition compared to Sham with improved scores at the post-training session. However, when Bonferroni correction for Type I Error was applied, only the effect for Digit Span Forward (see FIG. 1a) and Total Digit Span (see FIG. 1b) scores remained significant. This training effect for Digit Span Forward and Total Digit Span remained significant after accounting for baseline Digit Span performance. This was tested by re-running the Repeated Measures Analysis of Variance and including the baseline Digit Span scores as a covariate. A similar check of the finding was conducted using the Spielberger Trait and State Anxiety measures as covariates (each run in separate models); again, the results (triple interaction) or Digit Span Forward and Total Digit Span remained significant. On the Digit Span Forward test a total of 24 participants improved at least a 0.5 standard deviation relative to their baseline. Seven subjects showed no change and 8 showed a decline. The average number of digits improved relative to baseline was 0.73.

TABLE 4

Results from Repeated Measures Analysis of Variance Domain/Dependent Variable with Model Effects

| Verbal Episodic Memory | F | df | P Value |
|---|---|---|---|
| I. 1. HVLT - TOTAL RECALL | | | |
| Session | 14.05 | 1.37 | 0.001 |
| Session*Order | 0.824 | 1.37 | 0.37 |
| Training Condition | 3.37 | 1.37 | 0.074 |
| Training Condition*Order | 0.025 | 1.37 | 0.876 |
| Session* Training Condition | 0.011 | 1.37 | 0.916 |
| Session*Training Condition*Order | 0.42 | 1.37 | 0.521 |
| II. 2. HVLT - DELAYED RECALL | | | |
| Session | 2.09 | 1.37 | 0.156 |
| Session*Order | 5.22 | 1.37 | 0.028 |
| Training Condition | 4.7 | 1.37 | 0.037 |
| Training Condition*Order | 0.648 | 1.37 | 0.426 |
| Session* Training Condition | 1.2 | 1.37 | 0.267 |
| Session*Training Condition*Order | 2.01 | 1.37 | 0.164 |
| III. 3. HVLT - PERCENT RETENTION | | | |
| Session | 0.425 | 1.37 | 0.518 |
| Session*Order | 0.379 | 1.37 | 0.542 |
| Training Condition | 1.337 | 1.37 | 0.255 |
| Training Condition*Order | 0.046 | 1.37 | 0.832 |
| Session* Training Condition | 0.036 | 1.37 | 0.85 |
| Session*Training Condition*Order | 0.262 | 1.37 | 0.612 |
| IV. 4. HVLT - RECOGNITION DISCRIMINATION INDEX | | | |
| Session | 1.46 | 1.37 | 0.234 |
| Session*Order | 0.802 | 1.37 | 0.376 |
| Training Condition | 3.04 | 1.37 | 0.089 |
| Training Condition*Order | 0.02 | 1.37 | 0.887 |
| Session* Training Condition | 1.02 | 1.37 | 0.317 |
| Session*Training Condition*Order | 2.16 | 1.37 | 0.15 |
| V. VERBAL ASSOCIATIVE LEARNING | | | |
| VI. 1. VPA - TOTAL LEARNING | | | |
| Session | 10.925 | 1.37 | 0.002 |
| Session*Order | 10.064 | 1.37 | 0.003 |
| Training Condition | 7.274 | 1.37 | 0.01 |
| Training Condition*Order | 0.151 | 1.37 | 0.7 |
| Session* Training Condition | 8.98 | 1.37 | 0.005 |
| Session*Training Condition*Order | 6.975 | 1.37 | 0.012 |
| 2. VPA-Total Delayed Recall | | | |
| Session | 6.214 | 1.37 | 0.017 |
| Session*Order | 0.041 | 1.37 | 0.841 |
| Training Condition | 1.868 | 1.37 | 0.18 |
| Training Condition*Order | 0.119 | 1.37 | 0.732 |
| Session* Training Condition | 6.375 | 1.37 | 0.016 |
| Session*Training Condition*Order | 1.563 | 1.37 | 0.219 |
| 3. VPA-Learning Slope | | | |
| Session | 5.518 | 1.37 | 0.024 |
| Session*Order | 4.375 | 1.37 | 0.043 |
| Training Condition | 0.77 | 1.37 | 0.386 |
| Training Condition*Order | 2.852 | 1.37 | 0.1 |
| Session* Training Condition | 0.054 | 1.37 | 0.817 |
| Session*Training Condition*Order | 2.419 | 1.37 | 0.128 |
| 4. VPA-Percent Retention | | | |
| Session | 0.459 | 1.37 | 0.502 |
| Session*Order | 0.249 | 1.37 | 0.621 |
| Training Condition | 0.721 | 1.37 | 0.401 |
| Training Condition*Order | 1.147 | 1.37 | 0.291 |
| Session* Training Condition | 0.889 | 1.37 | 0.352 |
| Session*Training Condition*Order | 0.31 | 1.37 | 0.581 |
| 5. VPA-Delayed Recognition | | | |
| Session | 0.768 | 1.37 | 0.386 |
| Session*Order | 0.768 | 1.37 | 0.386 |
| Training Condition | 0.768 | 1.37 | 0.386 |
| Training Condition*Order | 0.768 | 1.37 | 0.386 |

TABLE 4-continued

Results from Repeated Measures Analysis of Variance
Domain/Dependent Variable with Model Effects

| Verbal Episodic Memory | F | df | P Value |
|---|---|---|---|
| Session* Training Condition | 0.768 | 1.37 | 0.386 |
| Session*Training Condition*Order | 0.768 | 1.37 | 0.386 |

VII.
VIII. VERBAL WORKING MEMORY

1. LN-Sequencing

| | | | |
|---|---|---|---|
| Session | 6.653 | 1.37 | 0.014 |
| Session*Order | 17.823 | 1.37 | 0 |
| Training Condition | 2.428 | 1.37 | 0.128 |
| Training Condition*Order | 0.282 | 1.37 | 0.599 |
| Session* Training Condition | 1.192 | 1.37 | 0.282 |
| Session*Training Condition*Order | 3.208 | 1.37 | 0.081 |

2. Digit Span (Backward)

| | | | |
|---|---|---|---|
| Session | 5.93 | 1.37 | 0.2 |
| Session*Order | 2.52 | 1.37 | 0.121 |
| Training Condition | 5.822 | 1.37 | 0.021 |
| Training Condition*Order | 0.355 | 1.37 | 0.555 |
| Session* Training Condition | 0.004 | 1.37 | 0.949 |
| Session*Training Condition*Order | 6.104 | 1.37 | 0.018 |

Attention/Concentration:

1. Digit Span (Forward)

| | | | |
|---|---|---|---|
| Session | 0.115 | 1.37 | 0.736 |
| Session*Order | 3.468 | 1.37 | 0.071 |
| Training Condition | 2.229 | 1.37 | 0.144 |
| Training Condition*Order | 1.365 | 1.37 | 0.25 |
| Session* Training Condition | 0.274 | 1.37 | 0.604 |
| Session*Training Condition*Order | 12.846 | 1.37 | 0.001 |

2. Total Digit Span

| | | | |
|---|---|---|---|
| Session | 3.481 | 1.37 | 0.07 |
| Session*Order | 5.161 | 1.37 | 0.029 |
| Training Condition | 6.673 | 1.37 | 0.014 |
| Training Condition*Order | 0.086 | 1.37 | 0.771 |
| Session* Training Condition | 0.226 | 1.37 | 0.609 |
| Session*Training Condition*Order | 14.988 | 1.37 | 0.001 |

Control Task:

Vocabulary

| | | | |
|---|---|---|---|
| Session | 1.114 | 1.37 | 0.298 |
| Session*Order | 1.735 | 1.37 | 0.196 |
| Training Condition | 0.51 | 1.37 | 0.48 |
| Training Condition*Order | 2.101 | 1.37 | 0.156 |
| Session* Training Condition | 0.438 | 1.37 | 0.512 |
| Session*Training Condition*Order | 0.001 | 1.37 | 0.971 |

The Analyses of Variance run on pre or post-test scores with Experimental Condition (MC Square, Sham) and Session (First, Second) as between-subject factors revealed a significant advantage for the MC Square device at post-training for the Hopkins Verbal Learning Test Delayed Recall (Wechsler, 1997,b) Letter Number Sequencing (Wechsler, D, 1997,b) Digit Span Forward (Wechsler, D, 1997,b) Backward (David Wechsler, 1997), and Total Score (Wechsler, D, 1997, b). After accounting for Type I error through the Bonferroni correction (28 tests), none remained significant. When we collapsed across the pre- and post-test scores and utilized their mean score, an advantage for performance under the MC Square device was evident on the Letter Number Sequencing task that was initially significant (p<0.05), but this effect became non-significant under Bonferroni Correction (14 tests).

Discussion

We conclude that there was a statistically reliable improvement on a measure of attention and concentration, the Digit Span Forwards test, following MC Square training. There was improvement on a measure of associative verbal learning and working memory in this initial analyses, but these findings did not survive Bonferroni correction. As expected the MC Square device had no influence on our control task involving vocabulary. The lack of an effect in most areas measured, including our control task, provided assurance that the MC Square was not having a general effect on cognitive activity and that when reliable change occurred it was a fairly specific effect. The training effect on Digit Span Forwards held true even after accounting for the participant's baseline level of Digit Span skill or their state and trait level of anxiety. A total of 24 out of 39 subjects (61.5%) showed at least a half standard deviation improvement (an increase of 0.73 digits, or approximately one digit) on the digit span task following training with the device. This increase may be of practical benefit in terms over holding on to more "heard" information over the short term.

In terms of performance on the individual tests, ignoring the training aspects of the study, participants using the MC Square Device subjects showed generally better performance on a working memory measure, the attention measure, and aspects of the associative learning test. However, here again these effects can only be considered trends as they were not statistically reliable after accounting for potential error rates (Type I error) that can occur when conducting multiple statistical tests.

The large number of tests conducted (14) certainly worked against obtaining statistically robust results that could remain significant after the stringent Bonferroni test. A Type II error, particularly in the case of the Associative Learning (Verbal Paired Associates, Total Recall) and Working Memory measures (Digits Backwards) was certainly possible. Initial analyses suggested an effect that was not sustained with Bonferroni correction. Note, in the repeated measures ANOVA examining the training effect for Verbal Paired Associates Total Recall the power present was 0.73. The power estimate for Digit Span Backwards was 0.67. Note, that the power for the training effect that did remain significant after Bonferroni correction, Digit Span Forwards, was 0.94. Therefore, power was at adequate levels and the relatively small sample size did not play as large a role in the loss of statistical significance as did the multiple tests and Bonferroni criteria. A larger sample size may show an effect for verbal learning, and further study is warranted.

We observed improvement in response to an AVE device on the same task, the digit span task, as did Budzynski and colleagues (Budzsynski, T. 1999). It is important to note that our effect was achieved with fewer training sessions. Also, our finding of increased attentional skill is interesting in light of previous results that suggest AVE devices can reduce inattention, impulsiveness, and reaction time in Attention Deficit Disorder children (Cohen & Doughles, 1972) (Joyce & Siever, 2000)

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES

Adrian, E. D., & Matthews, B. H. C. (1934). Potential changes from occipital lobes of man. *Brain*, 57, 355-385.

Budzinski, T., Budzinski, H., Sherlin, L., & Tang. (2002). Short and Long Term effects of Audio Visual Stimulation (AVS) on an Alzheimer's Patient as documented by Quantitative Electroencephalography (QEEG) and Low Resolution Electromagnetic brain Tomography(LORETA). *Journal of Neurotherapy*, 6(1).

Budzynski, T., Jordy, J., Budzynski, H., Tang, H., & Claypoole, H. (1999). Academic performance enhancement with photic stimulation and EDR feedback. *Journal of Neurotherapy*, 3(3), 11-21.

Budzynski, T. H., & Tang, J. (1998). *Biolight effects on the EEG* (SynchroMed report). Seattle, Wash.

Cohen, N., & Douglas, V. (1972). Characteristics of the orienting response in hyperactive and normal children. *Psychophysiology*, 9, 238-245.

David, N. (1997). PMS, EEG, and photic stimulation. *J. of Neurotherapy*, 2(2), 8-13.

Fox, P. T., & Raichle, M. E. (1985). Stimulus rate determines regional brain blood flow in striate cortex. *Annals of Neurology*, 17(3), 303-305.

Fried, R. (1993). What is theta? Biofeedback & Self-Regulation. 18, 53-58.

Gur, R. C., Gur, R. E., Obrist, W., Skolnick, B., & Reivich, M. (1987). Age and regional blood flow at rest and during cognitive activity. *Archives of General Psychiatry*, 44, 617-621.

Hagstadius, S., & Risberg, J. (1989). Regional cerebral blood flow characteristics and variations with age in resting normal subjects. *Brain and Cognition*, 10, 28-43.

Heiss, W. D., Pawlik, G., Holthoff, V., Kessler, J., & Szelies, B. (1992). PET correlates of normal and impaired memory functions. *Cerebrovascular and Brain Metabolism Reviews*, 4, 1-27.

Jason, B. (2001). *Hopkins verbal learning test-revised*. NY: Psychological assessment resources.

Jausovec, N. (1996). Differences in EEG alpha activity related to giftness. *Intelligence*, 23, 159-173.

Joyce, M., & Siever, D. (2000). Audio-visual entrainment program as a treatment for behavior disorders in a school setting. *Journal of Neurotherapy*, 4(2), 9-25.

Klimesh, W., Doppelmayr, M., Pachinger., & Ripper, B. (1997). Brain oscillations and human memory: EEG correlates in the upper alpha and theta band. *Neuroscience Letters*, 238, 9-12.

Kumano, H., Horie, H., Shidara, T., Kuboki, T., Suematsu, H., & Kindschi, C. L. (1996). Treatment of depressive disorder patient with EEG-driven photic stimulation. *Biofeedback and Self-Regulation*, 21, 323-334.

Magnan, A., Ecalle, J., Veuillet, E., & Collet, L. (2004). The effects of an audio-visual training program in dyslexic children. *Dyslexia.*, 10(2), 131-140.

Manns, A., Miralles, R., & Adrian, H. (1981). The application of audiostimulation and electromyographic biofeedback to bruxism and myofascial pain-dysfunction syndrome. *Oral Surgery*, 52(3), 247-252.

Meyer, J. S., Terayama, Y., & Takashima, S. (1993). Cerebral circulation in the elderly. *Cerebrovascular and Brain Metabolism Reviews*, 5, 122-146.

Nagahama, Y., Fukuyama, H., Yamauchi, H., Katsumi, Y., Magata, Y., Shibasaki, H., (1997). Age-related changes in cerebral blood flow activation during a Card Sorting Test. *Experimental Brain Research*, 114, 571-577.

Robert, A. Z. (2001). *Shipley institute of living scale*. LA.

Rosenfeld, P. (1997). EEG biofeedback of frontal alpha asymmetry in affective disorders. *Biofeedback,* 25(1), 8-12.

Sappey-Marinier, D., Calabrese, G., Fein, G., Hugg, J., Biggins, C., & Weiner, M. (1992). Effect of photic stimulation on human visual cortex lactate and phosphates using 1H and 31P magnetic resonance spectroscopy. *Journal of Cerebral Blood Flow and Metabolism,* 12(4), 584-592.

Schreiter-Gasser, U., Gasser, T., & Ziegler, P. (1993). Quantitative EEG analysis in early onset Alzheimer's disease: a controlled study. *Electroencephalography and Clinical Neurophysiolology,* 86, 15-22.

Spielberger, C. D., Gorsuch, R. L., & Lushene, R. E. (1970). *STAI Manual for the State Trait Anxiety Inventory*. Palo Alto, Calif.: Consulting Psychologists Press.

Tan, G., Kelly, J., & Calhoun, W. (1997). *Brain stimulation to improve cognition and mood of geriatric patients with dementia*. Paper presented at the Association for Applied Psychophysiology and Biofeedback, Sandiogo, Calif.

Wechsler, D. (1997). *Wechsler Memory Scale—Third Edition*. San Antonio, Tex.: Psychological Corporation.

Wechsler, D. (1997,b). *Wechsler Memory scale* (Third ed.). San antonio, Tex.: The Psychological corporation.

Zentall, S., & Zentall, T. (1976). Activity and task performance of hyperactive children as a function of environmental stimulation. *Journal of Consulting and Clinical Psychology,* 44(5), 693-697.

The above cited references are all hereby incorporated by reference in their entirety.

What is claimed:

1. A method to improve at least one of concentration, memory, cognitive performance, and stress-relief in a subject by audio-visual entrainment, the method comprising:
   a) selecting a subject in need of improvement in the at least one of concentration, memory, cognitive performance, and stress-relief;
   b) administering artificially synchronized flashes of light and pulsed tones to the subject, wherein the artificially synchronized flashes of light are in the frequency range of 4-12 Hz and wherein the artificially synchronized pulsed tones are in the frequency range of 4-12 Hz, and
   c) measuring of the at least one of concentration, memory, cognitive performance, and stress-relief in the subject,
   wherein the measurement of the at least one of concentration, memory, cognitive performance, and stress-relief in the subject is improved,
   wherein the flashes of light have a wavelength in the range of 400 to 720 nm and a brightness in the range of greater than 0 to less than or equal to 16 Lx, and
   wherein the flashes of light include a wave form with a varying frequency.

2. The method of claim 1, wherein the varying frequency includes at least one of an ascending frequency and a descending frequency.

3. The method of claim 1, wherein the flashes of light and pulsed tones are administered in-phase, out-phase, or a combination thereof,
   wherein in-phase administration of the flashes of light and pulsed tones comprises administration of flashes of light and pulsed tones on a left channel and a right channel at the same time, or
   wherein the out-phase administration of the flashes of light and pulsed tones comprises administration of flashes of light and pulsed tones on a left channel and a right channel at different times.

4. The method of claim 1, wherein administering the artificially synchronized flashes of light and pulsed tones occurs for a period of 15 to 60 minutes.

5. The method of claim 1, wherein administering the artificially synchronized flashes of light and pulsed tones for a period of 15 to 30 minutes.

6. The method of claim 1, wherein administering the artificially synchronized flashes of light and pulsed tones occurs daily for three or more days.

7. The method of claim 1, wherein the subject has been diagnosed with ADHD.

8. The method of claim 1, wherein the subject has been diagnosed with developmental impairment of executive function.

9. The method of claim 1, wherein the subject is suffering from age-related memory loss.

10. The method of claim 1, wherein the subject is at risk for age-related memory loss.

11. The method of claim 1, further comprising:
administering sounds of nature.

12. The method of claim 11, wherein the sounds of nature include at least one of river gurgling, birds chirping, rain drops, and ocean waves.

13. The method of claim 1 further comprising:
establishing a baseline score for the at least one of concentration, memory, cognitive performance, and stress-relief for the subject prior to administering the artificially synchronized flashes of light and pulsed tones; and
measuring an improved score for the at least one of concentration, memory, cognitive performance, and stress-relief for the subject after administering the artificially synchronized flashes of light and pulsed tones.

14. The method of claim 1 wherein stress-relief includes at least one of increasing relaxation, decreasing anxiety, and increasing restorative sleep.

15. A computer implemented method to improve at least one of concentration, memory, cognitive performance, and stress-relief in a subject by audio-visual entrainment, comprising:
on a computing device having one or more processors and a memory storing one or more programs for execution by the one or more processors, the one or more programs including instructions for:
administering synchronized flashes of light and pulsed tones to a subject in need of improvement in the at least one of concentration, memory, cognitive performance, and stress-relief, wherein the synchronized flashes of light are in the frequency range of 4-12 Hz and wherein the synchronized pulsed tones are in the frequency range of 4-12 Hz, and
measuring of the at least one of concentration, memory, cognitive performance, and stress-relief in the subject,
wherein the measurement of the at least one of concentration, memory, cognitive performance, and stress-relief in the subject is improved, and
wherein the flashes of light include a wave form with a varying frequency.

16. A computer system to improve at least one of concentration, memory, cognitive performance, and stress-relief in a subject by audio-visual entrainment, comprising:
one or more processors; and
memory configured to store:
one or more programs configured to be executed by the one or more processors, the one or more programs comprising instructions for:
administering synchronized flashes of light and pulsed tones to a subject in need of improvement in the at least one of concentration, memory, cognitive performance, and stress-relief, wherein the synchronized flashes of light are in the frequency range of 4-12 Hz and wherein the synchronized pulsed tones are in the frequency range of 4-12 Hz, and
measuring of the at least one of concentration, memory, cognitive performance, and stress-relief in the subject,
wherein the measurement of the at least one of concentration, memory, cognitive performance, and stress-relief in the subject is improved, and
wherein the flashes of light include a wave form with a varying frequency.

17. A non-transitory computer-readable storage medium storing one or more programs configured to be executed by one or more processing units at a computer comprising instructions for:
administering synchronized flashes of light and pulsed tones to a subject in need of improvement in at least one of concentration, memory, cognitive performance, and stress-relief, wherein the synchronized flashes of light are in the frequency range of 4-12 Hz and wherein the synchronized pulsed tones are in the frequency range of 4-12 Hz, and
measuring of the at least one of concentration, memory, cognitive performance, and stress-relief in the subject,
wherein the measurement of the at least one of concentration, memory, cognitive performance, and stress-relief in the subject is improved, and
wherein the flashes of light include a wave form with a varying frequency.

* * * * *